United States Patent [19]

Higuchi et al.

[11] Patent Number: 4,459,295
[45] Date of Patent: Jul. 10, 1984

[54] METHOD OF INCREASING ORAL ABSORPTION OF GLYCOSIDIC AND RELATED ANTIBIOTICS

[75] Inventors: Takeru Higuchi; Toshiaki Nishihata, both of Lawrence, Kans.

[73] Assignee: INTERx Research Corporation, Lawrence, Kans.

[21] Appl. No.: 387,409

[22] Filed: Jun. 11, 1982

Related U.S. Application Data

[63] Continuation-in-part of Ser. No. 213,123, Dec. 5, 1980, abandoned, which is a continuation-in-part of Ser. No. 128,100, Mar. 7, 1980, abandoned.

[51] Int. Cl.³ .............................................. A61K 31/71
[52] U.S. Cl. .................................... 424/232; 424/230; 424/231; 424/233; 424/234; 424/235; 424/317; 424/335
[58] Field of Search ............................... 424/230–235, 424/317, 335

[56] References Cited

FOREIGN PATENT DOCUMENTS 2258171 8/1975 France .

OTHER PUBLICATIONS

Gibaldi, M., et al., *J. Pharm. Sci.*, 62(2), 343–344 (1973).
Imamura, Y., et al., *Chem. Pharm. Bull.* (Japan), 22, 2324–2328 (1974).
Spector, R., et al., *J. Pharm. Exp. Ther.*, 188(1), 55–65 (1974).
Corell, T., et al. *Acta Pharmacol. et Toxicol.*, 45, 225–231 (1979).
Samejima, M., et al., *Yakugaku Zasshi*, 88(5), 618–622 (1968).
Sugimoto, I., et al., *Yakugaku Zasshi*, 88(6), 690–694 (1968).

*Primary Examiner*—Richard A. Schwartz
*Attorney, Agent, or Firm*—Manfred Polk; Michael C. Sudol, Jr.

[57] ABSTRACT

A method and drug form are provided for increasing the oral absorption of glycosidic and related antibiotics such as macrolide, aminoglycoside, lincomycin and anthracycline antibiotics and related chemical species by the oral administration of said glycosidic and related antibiotics in a suitable pharmaceutically accepted excipient to which has been added a hydroxyaryl or hydroxyaralkyl acid or salt thereof. The hydroxyaryl or hydroxyaralkyl acid or salt thereof is present in the drug form in quantities sufficient to be effective in enhancing the rate of oral absorption of glycosidic and related antibiotic.

12 Claims, No Drawings

METHOD OF INCREASING ORAL ABSORPTION OF GLYCOSIDIC AND RELATED ANTIBIOTICS

CROSS-REFERENCE TO RELATED APPLICATIONS

This application is a continuation-in-part of our previous application Ser. No. 213,123 filed Dec. 5, 1980 in the U.S. Patent and Trademark Office entitled "Method of Increasing Oral Absorption of Glycosidic and Related Antibiotics", now abandoned, which itself is a continuation-in-part of our previous application Ser. No. 128,100 filed Mar. 7, 1980 in the U.S. Patent and Trademark Office, entitled "Method of Increasing Oral Absorption of Glycosidic and Related Antibiotics", now abandoned, and incorporates all of that application including the co-pending applications mentioned therein.

BACKGROUND OF THE INVENTION

1. Field of the Invention

The present invention relates to the oral delivery of glycosidic and related antibiotics which by this route are poorly absorbed and more especially to the enhancement of this delivery by formulations which contain a hydroxyaromatic acid.

As employed in this application, the term "glycosidic and related antibiotics" refers to those antibiotics which contain a carbohydrate moiety which is attached through a glycosidic bond and includes such antibiotics as the macrolides, aminoglycosides, lincomycins and anthracyclines.

2. Description of the Prior Art

It is well known to the art that a number of antibiotic agents are only slowly absorbed from the gastrointestinal tract. Consequently, said antibiotic must be administered by the intravenous or intramuscular route or in excessively large oral doses in order to attain clinical efficacy. The $\beta$-lactam antibiotics is one class of antibiotic which is poorly absorbed by the oral route. Similarly, the glycosidic and related antibiotics, which are chemically characterized by a chemical structure which includes a carbohydrate moiety bonded to the remainder of the molecule by a glycosidic linkage, are poorly absorbed by the oral route. The glycosidic and related antibiotics, such as the macrolide, aminoglycoside, lincomycin, anthracycline and other chemically related antibiotics, are poorly absorbed from the gastrointestinal tract because of two properties, hydrophilicity and/or acid instability. The hydrophilic, polar nature of these antibiotics precludes their rapid absorption so that even the small percentage which is absorbed is subject to a long residency time in the gastrointestinal environment. It is therefore clear that any factor which enhances the rate of absorption will demonstrate improved clinical efficacy.

Many attempts have been made to improve the oral absorption of glycosidic and related antibiotics. Acid instability is partially overcome by coating the antibiotic with an acid stable-base labile enteric coating. This procedure has achieved some success with the acid labile, macrolide antibiotic, erythromycin; however, this procedure still does not allow complete absorption. Other approaches center on the reduction of the hydrophilicity of the glycosidic and related antibiotics by preparing chemical derivatives which are more lipophilic, see Murphy, Antibiotic Annual 1953–1954, page 500; Stephens, Antibiotic Annual 1958–1959, page 346; and Jones, Journal of Medicinal Chemistry, Volume 15, page 631, 1972. These lipophilic esters of erythromycin show enhanced blood levels when administered to warm-blooded animals.

The many attempts to enhance the oral absorption rate of glycosidic and related antibiotics have met with limited success with the macrolide antibiotics such as erythromycin and oleandomycin and with the lincomycin antibiotics. In these cases specialty coatings and lipophilic chemical derivatives have demonstrated improved absorption from the gastrointestinal tract, but in most cases absorption is incomplete. When similar techniques were applied to the aminoglycoside and anthracycline antibiotics, little or no oral absorption was reported. There is no oral dosage form for either of these two important classes of antibiotics.

Thus, there exists a clear and present need for a novel method to enhance the oral absorption rate of glycosidic and related antibiotics, particularly the macrolide antibiotics.

SUMMARY OF THE INVENTION

Accordingly, a major object of this invention is to provide a novel class of agents which enhance the oral absorption of glycosidic and related antibiotics particularly the macrolide antibiotics.

Another object is to provide a process utilizing said class of agents to enhance the oral absorption of glycosidic and related (macrolide) antibiotics.

Another object is to provide a stable drug form utilizing said class of agents which when administered orally will provide increased blood levels of the therapeutic agent.

Other objects, features and advantages of the invention will be apparent to those skilled in the art from the detailed description of the invention which follows.

All of the foregoing objects are readily attained by providing a method and drug form wherein the oral absorption of glycosidic and related antibiotics is enhanced, the method comprising the steps of preparing a drug form suitable for oral delivery, and a drug form comprising an effective unit dosage amount of the glycosidic or related antibiotic, a hydroxyaryl or hydroxyaralkyl acid or salt thereof, the latter adjuvants being present in said drug form in an amount sufficient to be effective in enhancing the rate of the oral absorption of the antibiotic and a suitable pharmaceutically accepted excipient.

DETAILED DESCRIPTION OF THE INVENTION

The present invention, generally comprises the steps of preparing a drug form capable of being orally administered, wherein the drug form comprises an effective unit dosage amount of a glycosidic or related antibiotic and a hydroxyaryl or hydroxyaralkyl acid or salt thereof, the hydroxyaryl or hydroxyaralkyl acid or salt thereof being present in the drug form in a sufficient quantity to be effective in enhancing the oral absorption rate and administering the drug form to warm-blooded animals. The amount of glycosidic and related antibiotic varies over a wide range, but generally any therapeutically effective unit dosage amount of the selected glycosidic or related antibiotic is used.

The hydroxyaryl or hydroxyaralkyl acids or their salts thereof that are used as the adjuvants in our method and in our drug forms have the following structural formulae including the various isomers possible within the formulae set forth:

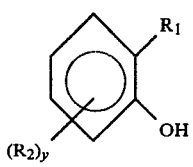

Formula I wherein $R_1$ is $CO_2H$, $—(CH_2)—COOH$,

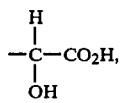

or a pharmaceutically acceptable salt thereof, particularly the sodium or calcium salt thereof,
wherein $R_2$ is OH, H, a lower alkoxy radical including methoxy, ethoxy, butoxy, or octyloxy, a lower alkyl radical including methyl, isopropyl, ethyl, t-butyl, n-butyl, or t-octyl, a halo radical, or a trihalo lower alkyl radical including trifluoromethyl, and
wherein y is an integer of 1 or 2.

More preferred adjuvants are those of Formula I wherein the $R_1$ and OH radicals are ortho to each other.

Specific adjuvants useful in our method and drug forms for enhancing oral absorption of the glycosidic and related (macrolide) antibiotics include 1. Sodium salicylate
2. Sodium-5-methoxysalicylate
3. 3-methylsalicylic acid
4. Sodium-5-chlorosalicylate
5. Sodium-5-bromosalicylate
6. 5-trifluorosalicylic acid
7. 3-t-butyl-5-methylsalicylic acid
8. Sodium-5-t-octylsalicylate
9. Sodium-3,5-diiodosalicylate
10. 5-n-butoxysalicylic acid
11. 5-methylsalicylic acid 2and
12. 3-t-butyl-6-methylsalicylic acid Such adjuvants are not considered novel per se and may be prepared by techniques known to those skilled in the art.

The amount of adjuvant of Formula I used in our method and drug forms should be a sufficient amount to be effective in enhancing the oral absorption rate of the drug from the gastro-intestinal compartment into the bloodstream, but generally the amount of adjuvant (Formula I) per unit dosage of the particular drug being administered is in the range of 50 mg to 750 mg. The amount of adjuvant to be effective will vary depending on the particular drug used and the release characteristics of the particular dosage form used (For example a rapidly disintegrating drug delivery device or a slow release device will have different adjuvant requirements).

Also the effectiveness of the adjuvant of Formula I becomes significant at a local concentration exceeding 0.01% at the absorption site. The use of adjuvants of Formula I whereby their concentration at the absorption site exceeds 5% is not recommended because of the local irritating effect on the tissue.

The glycosidic and related antibiotics whose enhanced oral delivery is a subject of the present invention encompass the macrolide antibiotics such as erythromycin, oleandomycin, spiramicin, berythromycin and kitasumycin, the lincomycin antibiotics such as lincomycin and clindamycin, the aminoglycosides such as gentamycin, kanamycin, neomycin, paromycin, streptomycin, tobramycin, viomycin, butirosin, sisomycin, netilmicin and the anthracyclines, daunamycin, doxorubicin and mithramycin.

The quantity of these glycosides or related antibiotics necessary for preparing the drug form could vary over a wide range, but would normally be regulated by that quantity necessary to comprise the therapeutically effective unit dosage.

The drug forms of this invention are suitably administered in oral dosage form, such as by tablet or capsule, by combining the glycosidic or related antibiotic in a therapeutic amount and the adjuvants of Formula I in a sufficient quantity to be effective to enhance oral delivery with an oral pharmaceutically acceptable inert carrier, such as lactose, starch (pharmaceutical grade), dicalcium phosphate, calcium sulfate, Kaolin, mannitol and powdered sugar. In order to reduce the irritation in the stomach, the preferred dose form of the adjuvant of Formula I should be a pharmaceutically acceptable salt and the drug form should be designed to release the glycosidic or related antibiotic and the hydroxyaryl or hydroxyaralkyl acid salt beyond the pylorus. In addition, when required, suitable binders, lubricants, disintegrating agents, and coloring agents can also be added. Typical binders include, without limitation, starch, gelatin, sugars such as sucrose, molasses, and lactose, natural and synthetic gums, such as acacia, sodium alginate, extract of Irish moss, carboxymethylcellulose, methylcellulose, and polyvinylpyrrolidone, polyethylene glycol, ethylcellulose and waxes. Typical lubricants for use in these dosage forms can include, without limitation, boric acid, sodium benzoate, sodium acetate, sodium chloride, leucine and polyethylene glycol. Suitable disintegrators can include, without limitation, starch, methylcellulose, agar, bentonite, cellulose and wood products, alginic acid, guar gum, citris pulp, carboxymethylcellulose, and sodium lauryl sulfate. Optionally, if desired, a conventionally, pharmaceutically acceptable dye can be incorporated into oral dosage unit form, e.g., any of the standard FD & C dyes.

EXAMPLE I

Typical preparation of enteric-coated tablets containing adjuvant

Compressed erythromycin lactobionate tablets were prepared according to standard tablet compression techniques. The tablets contained 391 mg erythromycin lactobionate, 300 mg salicylic acid, 200 mg sodium bicarbonate, 200 mg Avicel PH 101, 100 mg Starx Starch and 36 mg Lubratab. The tablets were precoated with 16 mg hydroxypropylmethylcellulose and enterically coated with 49 mg hydroxypropylmethylcellulose phthalate. The total tablet weight, including coating, was 1292 mg.

Oral formulations for gentamicin sulfate were prepared by dry-filling hard gelatin capsules with 300 mg gentamicin sulfate and 300 mg sodium-5-methoxysalicylate. The capsules were enterically coated with 25 mg hydroxypropylmethylcellulose and 65 mg hydroxypropylmethylcellulose phthalate. Total capsule weight, including coating, was 790 mg.

EXAMPLE II

The following drugs and adjuvants of Formula I were tested orally in a dog with the following protocol and results.

The oral dosage forms were administered to adult beagle dogs (9–15 kg) which had been fasted overnight (16–18 hours). Blood samples (0.7 ml) were collected at 30, 60, 90, 120, 150, 180, 240, 300 and 360 minutes. The serum was isolated from each blood sample and stored at −20° C. until being assayed within two weeks. Serum levels of erythromycin and gentamicin were determined by standard microbiological assay techniques against the appropriate susceptible organisms. The area under the serum concentration curve for each dog experiment was determined by a summation of successive trapezoidal areas extrapolated from the last sampling time point to the time at which the serum concentration equalled the sensitivity limit of the assay. The percent of drug absorbed was determined by comparing the area under the oral serum concentration curve to the area under an intravenous serum concentration curve in the same animal.

The summary protocol for the dog model test was as follows:

Animals used: Adult beagle dogs, male and female (9–15 kg).
Anesthesia: None
Blood Sampling: 0.6 ml from the leg vein at 15, 30, 45, 60, 90, 120, 180 and 240 minutes.

$$\frac{(AUC)\text{rectal } (Dose)\text{i.v.}}{(AUC)\text{i.v. } (Dose)\text{rectal}} \times 100$$

AUC means and the (AUC)i.v. was determined for each individual dog for each drug.

For the above test a compressed tablet or gelatin capsule which was enteric coated was used.

The drug concentration was 200 mg/dog unless otherwise noted and the adjuvant (compound of Formula I) concentration was 300 mg/dog unless otherwise noted.

| | RESULTS | | |
|---|---|---|---|
| | No Adjuvant | Adjuvant | |
| Drug | Control | 1 | 2 |
| Gentamicin sulfate | 9%* | — | 30% |
| Erythromycin | 29% | 50% | — |

1 - Sodium Salicylate
2 - Sodium-5-methoxysalicylate
*% bioavailability

Any skilled artisan concerned with the subject matter of this invention can prepare these oral dosage forms by simply referring to the oral dosage form preparatory procedure outlined in REMINGTON'S PHARMACEUTICAL SCIENCES, Fifteenth Edition (1975), pages 1576 through 1617 inclusive.

From the foregoing description, one of ordinary skill in the art can easily ascertain the essential characteristics of this invention, and without departing from the spirit and scope thereof, can make various changes and modifications of the invention to adapt it to various usages and conditions. As such, such changes and modifications are properly, equitably, and intended to be, within the full range of the equivalence of the following claims.

What is claimed is:

1. A method for enhancing the rate of absorption of an orally administered glycosidic or related antibiotic into the bloodstream, said method comprising the steps of preparing a drug form capable of being orally absorbed, said drug form comprising a therapeutically effective dosage amount of the glycosidic or related antibiotics and an adjuvant of the Formula:

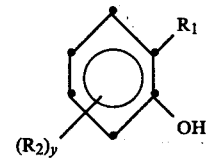

wherein $R_1$ is $-CO_2H$, $-(CH_2)-COOH$,

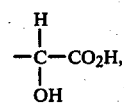

$SO_3H$ or a pharmaceutically acceptable salt thereof, wherein $R_2$ is OH, H, a lower alkoxy radical, a lower alkyl radical, a halo radical, or a tri-halo lower alkyl radical, and wherein y is an integer of 1 or 2;

said adjuvant being present in said drug form in a sufficient amount to be effective in enhancing said oral absorption rate and administering said drug form orally to a warm-blooded animal.

2. The method of claim 1 wherein said glycosidic or related antibiotic is a macrolide, an aminoglycoside, lincomycin, clindamycin or anthracycline.

3. The method of claim 2 wherein said macrolide is erythromycin.

4. The method of claim 2 wherein said aminoglycoside is gentamycin.

5. The method of claim 1 wherein said adjuvant comprises

Sodium salicylate
Sodium-5-methoxysalicylate
3-methylsalicylic acid
Sodium-5-chlorosalicylate
Sodium-5-bromosalicylate
5-trifluorosalicylic acid
3-t-butyl-5-methylsalicylic acid
Sodium-5-t-octylsalicylate
Sodium-3,5-diiodosalicylate
5-n-butoxysalicylic acid
5-methylsalicylic acid or
3-t-butyl-6-methylsalicylic acid 6. The method of claim 1 wherein the adjuvant is salicylic acid, sodium salicylate or sodium 5-methoxysalicylate.

7. An orally administered drug form comprising a therapeutically effective amount of glycosidic or related antibiotic and an adjuvant comprising a compound of the formula:

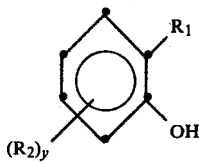

wherein $R_1$ is $-CO_2H$, $-(CH_2)-COOH$,

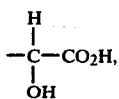

$SO_3H$, or a pharmaceutically acceptable salt thereof wherein $R_2$ is OH, H, a lower alkoxy radical, a lower alkyl radical, a halo radical, or a tri-halo lower alkyl radical, and wherein y is an integer of 1 or 2;

said adjuvant being present in said drug form in sufficient amount to be effective in enhancing the oral absorption rate of said glycosidic or related antibiotic.

8. The drug form of claim 7 wherein said glycosidic or related antibiotic is macrolide, aminoglycoside, lincomycin, clindamycin or anthracycline.

9. The drug form of claim 8 wherein said macrolide is erythromycin.

10. The drug form of claim 8 wherein said aminoglycoside is gentamicin.

11. The drug form of claim 7 wherein said adjuvant comprises:
Sodium salicylate
Sodium-5-methoxysalicylate
3-methylsalicylic acid
Sodium-5-chlorosalicylate
Sodium-5-bromosalicylate
5-trifluorosalicylic acid
3-t-butyl-5-methylsalicylic acid
Sodium-5-t-octylsalicylate
Sodium-3,5-diiodosalicylate
5-n-butoxysalicylic acid
5-methylsalicylic acid or
3-t-butyl-6-methylsalicylic acid 12. The drug form of claim 11 wherein the adjuvant is salicylic acid, sodium salicylate or sodium 5-methoxysalicylate.

* * * * *